(12) United States Patent
Getto

(10) Patent No.: US 12,053,486 B2
(45) Date of Patent: Aug. 6, 2024

(54) COMPOSITIONS FOR THE TREATMENT OF INFECTIONS IN FEET

(71) Applicant: Therazure LLC, Hackettstown, NJ (US)

(72) Inventor: Jason Getto, Hackettstown, NJ (US)

(73) Assignee: Therazure LLC, Hackettstown, NJ (US)

( * ) Notice: Subject to any disclaimer, the term of this patent is extended or adjusted under 35 U.S.C. 154(b) by 0 days.

(21) Appl. No.: 15/917,337

(22) Filed: Mar. 9, 2018

(65) Prior Publication Data

US 2019/0275078 A1    Sep. 12, 2019

(51) Int. Cl.

| A61K 33/34 | (2006.01) |
| A61K 31/19 | (2006.01) |
| A61K 33/00 | (2006.01) |
| A61K 33/06 | (2006.01) |
| A61K 33/24 | (2019.01) |
| A61K 36/88 | (2006.01) |
| A61K 47/36 | (2006.01) |
| A61P 31/04 | (2006.01) |

(52) U.S. Cl.
CPC ............. *A61K 33/34* (2013.01); *A61K 31/19* (2013.01); *A61K 33/00* (2013.01); *A61K 33/06* (2013.01); *A61K 33/24* (2013.01); *A61K 36/88* (2013.01); *A61K 47/36* (2013.01); *A61P 31/04* (2018.01)

(58) Field of Classification Search
CPC ........ A61K 33/34; A61K 31/19; A61K 33/00; A61K 33/06; A61K 33/24; A61K 36/88; A61K 47/36; A61K 9/0014; A61K 47/02; A61P 31/04
See application file for complete search history.

(56) References Cited

U.S. PATENT DOCUMENTS

| 2,014,005 | A |   | 9/1935  | Mershon |
| 4,268,504 | A |   | 5/1981  | Harrington et al. |
| 4,859,694 | A |   | 8/1989  | Pavlich |
| 4,935,058 | A | * | 6/1990  | Helmstetter ............ C04B 28/26 106/14.44 |
| 5,100,868 | A |   | 3/1992  | Snyder et al. |
| 5,120,703 | A |   | 6/1992  | Snyder et al. |
| 5,157,015 | A |   | 10/1992 | Snyder et al. |
| 5,780,064 | A |   | 7/1998  | Meisters et al. |
| 6,124,221 | A |   | 9/2000  | Gabbay |
| 6,133,318 | A |   | 10/2000 | Hart |
| 6,346,281 | B1 |   | 2/2002  | DeAth et al. |
| 6,383,923 | B1 |   | 5/2002  | Brown et al. |
| 6,482,424 | B1 |   | 11/2002 | Gabbay |
| 6,767,552 | B2 |   | 7/2004  | Narang |
| 6,846,498 | B2 |   | 1/2005  | DeAth et al. |
| 6,942,875 | B2 |   | 9/2005  | Hedgpeth |
| 7,124,832 | B2 |   | 10/2006 | Kelly |
| 7,250,181 | B2 |   | 7/2007  | Ghosal |
| 7,296,690 | B2 |   | 11/2007 | Gabbay |
| 7,537,063 | B2 |   | 5/2009  | La Croix |
| 7,842,313 | B2 |   | 11/2010 | Pound et al. |
| 7,854,946 | B1 |   | 12/2010 | Hillwig |
| 8,188,085 | B2 |   | 5/2012  | Greenlee et al. |
| 8,349,365 | B2 |   | 1/2013  | Yamasaki et al. |
| 8,371,391 | B2 |   | 2/2013  | La Croix |
| 8,389,581 | B2 |   | 3/2013  | DeMarco et al. |
| 8,505,162 | B2 |   | 8/2013  | Pigg et al. |
| 8,507,674 | B2 |   | 8/2013  | Suga et al. |
| 8,586,102 | B2 |   | 11/2013 | Rocker et al. |
| 8,722,727 | B2 |   | 5/2014  | Greenlee et al. |
| 8,986,747 | B2 |   | 3/2015  | Allen |
| 9,018,262 | B2 |   | 8/2015  | DeMarco et al. |
| 9,107,418 | B2 |   | 8/2015  | Smithyman et al. |
| 9,393,342 | B2 |   | 7/2016  | Joseph et al. |
| 9,403,041 | B2 |   | 8/2016  | Gabbay |
| 9,474,282 | B2 |   | 10/2016 | Hall |
| 9,499,593 | B2 |   | 11/2016 | Malley et al. |
| 9,713,632 | B2 |   | 7/2017  | Van Der Weerden et al. |
| 9,732,071 | B2 |   | 8/2017  | Patron et al. |
| 9,750,245 | B2 |   | 9/2017  | Lemire et al. |
| 2004/0019112 | A1 |   | 1/2004  | Maley |
| 2004/0062742 | A1 |   | 4/2004  | Winston et al. |
| 2004/0175433 | A1 | * | 9/2004  | Thomson ............ A61K 9/0017 424/630 |
| 2008/0311222 | A1 |   | 12/2008 | Pound |
| 2009/0191137 | A1 |   | 7/2009  | Vempati et al. |
| 2009/0204187 | A1 | * | 8/2009  | Mankovitz ............ A61K 31/19 607/88 |

(Continued)

FOREIGN PATENT DOCUMENTS

| CN | 104645539 |   | 5/2015 |
| CN | 104645539 A | * | 5/2015 |

(Continued)

OTHER PUBLICATIONS

The International Search Report and Written Opinion, issued on Jun. 28, 2019, in the corresponding PCT Application No. PCT/US19/20542.

(Continued)

*Primary Examiner* — David Browe

(57) ABSTRACT

Compositions for the treatment of microbial infections and for the general well-being of a mammals' skin, nails, hooves, claws and/or feet, including a blend of copper sulfate, water, and at least one clay or clay-like material, methods for making such compositions, and methods for the use of such compositions to control, treat, prevent microbial infections of the same.

1 Claim, No Drawings

(56) References Cited

U.S. PATENT DOCUMENTS

| | | | |
|---|---|---|---|
| 2009/0232892 A1 | 9/2009 | Yamasaki et al. |
| 2010/0239679 A1 | 9/2010 | Greene et al. |
| 2010/0256369 A1 | 10/2010 | Suga et al. |
| 2010/0260866 A1 | 10/2010 | Lu |
| 2011/0027420 A1 | 2/2011 | Mehansho |
| 2014/0005139 A1 | 1/2014 | Yamasaki et al. |
| 2015/0183708 A1 | 7/2015 | Harris et al. |
| 2016/0108096 A1 | 4/2016 | Thompson et al. |
| 2016/0330976 A1 | 11/2016 | Mitter et al. |
| 2016/0338360 A1 | 11/2016 | Mitter et al. |
| 2016/0376263 A1 | 12/2016 | Patron et al. |
| 2017/0087199 A1 | 3/2017 | Patron et al. |
| 2017/0096418 A1 | 4/2017 | Patron et al. |
| 2018/0021374 A1 | 1/2018 | Tuba |

FOREIGN PATENT DOCUMENTS

| | | | |
|---|---|---|---|
| CN | 107698217 A | * | 2/2018 |
| WO | 02/39963 A1 | | 5/2002 |

OTHER PUBLICATIONS

USDA. "Copper Sulfate Livestock." USDA National Organic Program, Feb. 12, 2015. https://www.ams.usda.gov/sites/default/files/media/Copper%20Sulfate%203%20TR%202015.pdf.

Fioravanti, Kayla. "A Closer Look at Sodium Hydroxide." Personal Care: Information Based on Scientific Facts, Personal Care Truth, Apr. 26, 2011, personalcaretruth.com/2011/04/a-closerlook-at-sodium-hydroxide/.

Zelman, Kathleen. "Stabilizers, Thickeners and Gelling Agents." Food Nutrition Magazine, Academy of Nutrition Dietetics, Nov. 30, 2017, foodandnutrition.org/may-june2017/stabilizers-thickeners-gelling-agents/.

Guerrera et al. "Therapeutic Uses of Magnesium." AAFP, American Academy of Family Physicians, Jul. 15, 2009, www.aafp.org/afp/2009/0715/p157.html#.

Ishler. 'Prevention and Control of Foot Problems in Dairy Cows', Penn State Extension, Feb. 11, 2016, extension.psu.edu/prevention-and-control-of-foot-problems-in-dairy-cows.

"Everyday Chemicals: Acetic Acid—Vinegar & Volcanoes." Compound Interest, Jun. 12, 2015, www.compoundchem.com/2015/06/11/acetic-acid/.

Horse Journal. "Hoof Packing Power." Expert Advice on Horse Care and Horse Riding, Cruz Bay Publishing, May 1, 2007, www.equisearch.com/articles/hoof-packing-power.

Quiroga et al. "The Effects of Aggregates Characteristics on the Performance of Portland Cement Concrete." International Center for Aggregates Research, Aug. 2004.

Letscher-Bru V et al: "Antifungal Activity of Sodium Bicarbonate Against Fungal Agents Causing Superficial Infections", Mycopathologia, Kluwer Academic Publishers, DO, vol. 175, No. 1-2, Sep. 19, 2012, pp. 153-158, XP035169812.

Laura G Corral et al: "Antimicrobial Activity of Sodium Bicarbonate", Journal of Food Science, vol. 53, No. 3, May 1, 1988, pp. 981-982, XP055534903.

The extended European search report, mailed on Oct. 29, 2021, in the related European Appl. No. 19763331.6.

* cited by examiner

COMPOSITIONS FOR THE TREATMENT OF INFECTIONS IN FEET

FIELD OF THE INVENTION

The invention relates to antimicrobial compositions. The invention further relates to compositions for treatment of antimicrobial infections that affect the feet of animals, i.e., the skin, nails, claws and/or hooves of animals. The invention further comprises compositions for antimicrobial and dermatological uses for mammals. The invention further comprises methods of preparing such compositions.

BACKGROUND OF THE INVENTION

There are many antimicrobial infections that effect the skin, nails, claws and/or hooves of various mammals. For example, thrush is an unpleasant infection common to hooved animals identified by a horrid odor of rotting flesh and black liquid oozing from the infected area. It most often involves the bacteria *Fusobacterium necrophorum* (also known as *Spherophorus necrophorus*), but can also be caused by certain pathogenic fungi. In horses, it is present in and around the horse's frog. Thrush can be aggressive, destroying the frog and exposing deeper tissue in the foot of the horse which can cause lameness. Environmental conditions can accelerate the severity of a thrush infection. The bacteria linked to thrush thrive in moist or wet, dirty ground conditions, which can be further exacerbated by the manure and urine in horse stables or pasture.

Another example of a microbial infection that effects the hooves of animals is hoof rot, also known as foot rot or pododermatitis. Hoof rot is a bacterial infection that harms the area between the two toes of the affected animal. It is extremely painful and contagious. If not treated properly it can infect whole herds, *Fusohacterium necrophorum* and *Bacteroides melaninogenicus* are bacterium that cause hoof rot. *Dichelobacter nodosus* may also play a role in the disease in some animals. These bacteria are common to the environment in which the animals live.

Another example is paronychia which causes the skin around the nail or claw in canines to become red, inflamed, and warm to the touch. The cause of the infection can be bacterial in nature or a type of fungus called *Candida*. Another common canine infection is the fungal infection onychomycosis, which develops in the nail bed and occurs due to exposure to different types of fungi, molds and bacteria.

Another example is onychomycosis, also known as *Tinea ungnium*, which is a fungal infection that affects either the fingernails or toenails of humans. Nail fungal infections are commonly caused by a group of fungi called dermnatophytes, such as *Candida*. It is also possible that the infection is caused by some yeasts such as *Trichoohyton rubrum, Trichophytron interdigitale, Epidermophyton floccosum, Trichophyton tonsurans*, or *Trichophyton soudanense*, or molds such as *neoscytaidium, scopulariopsis*, or *aspergiilus*. Humans who have diabetes, athlete's foot, or a weak immune system, who smoke, or whose family members are prone to these infections, are at a higher risk of developing these fungal infections.

Another example is laminitis which is caused by repeated physical trauma to the feet of animals during e.g. endurance riding, driving, or jumping on hard ground. It can also be caused by overenthusiastic hoof trimming or be triggered by sickness. Severe lameness in one limb will cause a horse or pony to carry excessive weight on his other limbs, which may cause laminitis, Typically ice is used to cool and reduce the inflammation in laminitic horses via ice boots, however, the hoof usually becomes softer as the ice melts creating a dangerous situation due to the already rotating bones in the hoof. A soft hoof is the worst thing for a foundering horse with laminitis. An embodiment of the present invention provides the cooling effect while actually keeping the hoof hard.

Another example is furunculosis, which is an infection of a hair follicle most commonly caused by bacteria. The infection forms a furuncle, also known as a boil or a cyst. An embodiment of the present invention cured a furuncle also known as an interdigital cyst in a dog.

The above conditions can be treated by scrubbing the infected area clean and/or treating with a liquid solution of dilute iodine, antibiotic medication, or other antiseptic. There are also oral antifungal medications to treat these infections. Most of these oral treatments are used to treat nail fungal infections in humans. These treatments can take up to 4 months before fully replacing the infected nail with uninfected nail. In some extreme cases, a physician will opt to remove the entire nails or claw.

It is known that copper sulfate has antimicrobial properties. To date, it is used in liquid form alone or together with other antimicrobial agents or as a powder.

Once an animal is treated with the existing liquid antimicrobial compositions, it must then be kept in a clean, dry environment and the antimicrobial solution must be applied on a regular basis until the infection's symptoms have disappeared and the damaged tissues are heeled. For cattle or dairy cows, foot baths containing copper sulfate or other antimicrobial agents are often used for treatment. This is also ineffective as the liquid solution quickly dries when it comes into contact with bedding such as shavings or straw in stalls. The same happens in pasture areas when the hoof makes contact with dirt. The worst scenario occurs when the treated hooves come in contact with manure or urine that not only ends treatment, but re-infects the area with new bacteria or other thrush inducing agents.

U.S. Pat. No. 8,505,162 describes a method of treating thrush by utilizing an adherent, rapidly curing synthetic organic resin and a microbial agent such as copper sulfate. This composition requires curing the synthetic organic resin and does not provide a practical, easy to use solution for treating thrush.

U.S. Patent Application 20150164946 describes a composition for treating thrush made of copper sulfate in a water or viscous base, as well as chlorhexidine salt. The composition does not allow for packing or provide a barrier against the damp, dirty conditions found in a stall, pasture or stable.

U.S. Patent Application 20050121205 describes a method and apparatus for in situ and molded horseshoeing. A method of applying copper sulfate to the foot infected with thrush is described. The copper sulfate is in the form of a powder. A cotton ball is then put on top and the foot packed with liquid material. This does not describe the composition contained herein.

The current treatments, including the treatment examples referred to above, are not practical, and in the case of foot baths, are not often possible. What is needed is a medicament that can treat the existing infection as well as protect the foot from further infection and from the moist, damp conditions in the animal's living environment. A treatment is needed that can be applied or packed into the nail, foot, claw or hoof, providing longer-lasting protection without multiple applications and change in environment, one in which a nail, foot, claw or hoof can come into contact with moisture whether it be manure, urine and other wet organic matter, but remain dry, with little exposure to additional microbial organisms.

SUMMARY OF THE INVENTION

The present invention provides a composition for the treatment of microbial infections in nails, feet, claws and hooves of mammals and methods of making the same. The present invention, in one embodiment, is a compact material that can be utilized as a packing material to treat a bacterial infection as well as keep moisture and organic material that may contain additional bacteria from entering the infected area. The present invention, in another embodiment, is a composition that can be applied topically to treat microbial infections of the nails, claws and/or hooves of mammals. In one embodiment, copper sulfate, clay, water, sodium bicarbonate and acetic acid are utilized in approximately equal parts. This embodiment is not in liquid for and therefore does not dry or dissipate into a wet, dirty stall following its application to the affected foot, claw or hoof. The present invention is a composition comprising an antimicrobial medicament and a naturally occurring clay suitable for pharmaceutical use. The present invention may also include an acid, a stabilizer, and/or a thickening agent.

The advantages and features of the present invention and methods for attaining them will become more apparent from the embodiments that are described in detail below. The present invention is not limited to the embodiments disclosed herein, but may be embodied in various forms. The embodiments are provided to fully convey the scope of the present invention to those skilled in the art to which the invention pertains.

Definitions

When the articles "a," "an," "one," "the," and "said" are used herein, they mean "at least one" or "one or more" unless otherwise indicated.

The term "animal" encompasses any non-human animal. For example, where the term "animal" is used herein, the animal can be, for example, a sheep, goat, cow, pig, deer, alpaca, bison, camel, donkey, horse, mule, llama, rabbit, dog, and/or cat.

The term "mammal" encompasses animals as described above and humans.

The terms "comprising," "including," and "having" are intended to be inclusive and mean that there may be additional elements other than the listed elements.

The term "effective amount" refers to a quantity which is sufficient to achieve the desired result.

The term "form holding ability" refers to the ability of a composition to adhere to the infected area.

DESCRIPTION OF THE INVENTION

The present invention provides a composition for the prevention or treatment of microbial infections in the nails, skin, feet, claws and hooves of mammals. More specifically, the present invention provides a treatment of the infections caused by *Fusobacterium necrophorum*, *Candida*, *Pseudomonas aeruginosa*, and some species of *Staphylococcus*. The composition in one embodiment is in the form of a solid, or semi-solid and not a liquid. The composition may also be in the form of a paste, gel, or ointment. The composition of the present invention comprises copper sulfate, clay, and water. The composition may also comprise sodium bicarbonate, acetic acid, as well as xanthan gum.

For the copper sulfate, it is preferable to use copper sulfate pentahydrate. The water may be from any source, but in a preferred embodiment it is distilled or purified water.

Examples of the clay include any naturally occurring clay suitable pharmaceutical use. Preferred embodiments include kaolin, bentonite, Fuller's Earth, sea clay, rhassoul clay, arrow root powder, titanium dioxide, zeolite clay, diatomaceous earth, cramp bark powder, sodium borate, red (Moroccan) clay, green (French) clay, and any other veterinary suitable clay.

Though sodium bicarbonate is the preferred base, other substances can be used such as sodium acetate; potassium bicarbonate, sodium borate, [may be sodium hydroxide], zinc oxide, lead oxide, aluminum oxide, stannous oxide, beryllium hydroxide, and other amphoteric hydroxides.

In addition to the clay, copper sulfate, sodium bicarbonate and water, acetic acid is preferably added to the solution. Vinegar may be used as the source of acetic acid for ease of providing the acetic acid in a proportion acceptable for use in a medicament. Vinegar is readily available and provides an appropriate proportion of the acetic acid that is acceptable for use in topical therapeutic agents. It is also stable as an ingredient. Other week acids such can be used as citric acid, tartaric acid, succinic acid, lactic acid or dilute hydrochloric acid to name a few acceptable substitutes.

In yet another embodiment, a stabilizer is added to the composition. One example of a readily available stabilizer is xanthan gum. Other stabilizers suitable for medicinal compositions may be utilized such as guar gum, agar, soy lecithin, mustard, egg yolk, sodium phosphates, sodium stearoyl lactylate, DATEM, emulsifying wax, cetearyl alcohol, polysorbate 20, ceteareth 20, carrageenan, petroleum jelly, and paraffin wax.

In yet another embodiment, a thickening agent is also incorporated, such as potassium bitartrate, corn starch, common baking flour, arrowroot, katakuri starch, potato starch, sago, tapioca, alginin, guar gum, locust bean gum, and xanthan gum. Other embodiments may include emulsifiers, gelling agents, humectants, anticaking agents, and coating agents.

In yet another embodiment, a moisturizing agent is also incorporated, such as mineral oil or glycerin.

Another embodiment of the invention includes a cream form for use on the epidermis of mammals, including the outside of the hooves of animals and skin and nails of humans.

In order to provide a therapeutic cream application according to the invention, magnesium sulfate can be added. Magnesium sulfate can be used as the source of magnesium sulfate.

Another embodiment of the invention includes a liquid form for use as an antiseptic and/or shampoo.

Example 1 Packing Composition

Two quarts of powdered bentonite clay were combined with two quarts of copper sulfate, pentahydrate. To that mixture, two quarts of sodium bicarbonate were added. The resulting powder was thoroughly mixed. Two quarts of vinegar were slowly added while rapidly stirring throughout the entire visible chemical reaction of the powder ingredients with the liquid. Once the substance was completely mixed and the visible chemical reaction weakens, two quarts of tap water were also poured slowly while again rapidly stirring until the mixture was consistent and all ingredients mixed. The mixture was then refrigerated for storage. A sufficient amount of the packing composition of example 1 was then applied to cover the infected area until the infection goes away.

Example 2 Packing Composition

The method described in Example 1 was followed with the exception that kaolin clay powder was incorporated instead of bentonite clay powder. The result was a similar, but slightly softer composition. To enhance this formula, xanthan gum was added in an amount of one tablespoon per quart of mixture and mixed into the composition. The embodiment of this Example 2 was as effective as that of Example 1 when applied shortly after mixture.

Example 3 Packing Composition

The method described in Example 1 was followed with the exception that Fuller's Earth Formula was incorporated instead of bentonite clay powder. The result was a similar composition. The embodiment of this Example 3 did not have the same form holding ability as that of Example 1 but was as effective at treating thrush when applied shortly after mixture.

Example 4 Packing Composition

The method described in Example 1 was followed with the exception that Sea Clay was incorporated instead of bentonite clay powder. The result was a similar composition.
The embodiment of this Example 4 was as effective as that of Example 1 when applied shortly after mixture.

Example 5 Packing Composition

The method described in Example 1 was followed with the exception that rhassoul clay was incorporated instead of bentonite clay powder. The result was a similar composition except that it did not hold as much moisture. The embodiment of this Example 5 was as effective as that of Example 1 when applied shortly after mixture.

Example 6 Packing Composition

The method described in Example 1 was followed with the exception that titanium dioxide powder was incorporated instead of bentonite clay powder. One teaspoon of xanthan gum per pint of the resulting mixture was added. The result was a similar composition. The embodiment of this Example 6 was as effective as that of Example 1 when applied shortly after mixture.

Example 7 Packing Composition

The method described in Example 1 was followed with the exception that arrowroot powder was incorporated instead of bentonite clay powder. One teaspoon of xanthan gum per pint of the resulting mixture was added. The result was a similar composition.
The embodiment of this Example 7 was as effective as that of Example 1 when applied shortly after mixture.

Example 8 Packing Composition

The method described in Example 1 was followed with the exception that zeolite clay was incorporated instead of bentonite clay powder. One teaspoon of xanthan gum per pint of the resulting mixture was added. The result was a similar composition. The embodiment of this Example 8 was as effective as that of Example 1 when applied shortly after mixture.

Example 9 Packing Composition

The method described in Example 1 was followed with the exception that diatomaceous earth was incorporated instead of bentonite clay powder. Approximately one teaspoon of xanthan gum per pint of the resulting mixture was added. The result was a similar composition. The embodiment of this Example 9 was as effective as that of Example 1 when applied shortly after mixture.

Example 10a Packing Composition

The method described in Example 1 was followed with the exception that cramp bark powder was incorporated instead of bentonite clay powder. This formula produced a dry product that lacked the moisture of previous formulas. Approximately one teaspoon of glycerin per pint was added and mixed in. The result was a composition similar to that of Example 1. The embodiment of this Example 10a was as effective as that of Example 1 when applied shortly after mixture.

Example 10b Packing Composition

The method described in Example 10 was followed with the exception that one teaspoon of mineral oil per pint of the resulting mixture was added. The result was a similar composition. The embodiment of this Example 10b was as effective as that of Example 1 when applied shortly after mixture.

Example 11a Packing Composition

The method described in Example 1 was followed with the exception that sodium borate was incorporated instead of bentonite clay powder. This formula produced a dry product that lacked the moisture. One teaspoon of glycerin per pint of the resulting mixture was added. The result was similar to the composition of Example 1 but had a bad odor. The embodiment of this Example 11a was as effective as that of Example 1 when applied shortly after mixture.

Example 11b Packing Composition

The method described in Example 11a was followed with the exception that one teaspoon of mineral oil per pint of the resulting mixture was added. The result was a similar composition that was not as odoriferous as Example 11a. The embodiment of this Example 11b was as effective as that of Example 1 when applied shortly after mixture.

Example 12a Packing Composition

The method described in Example 1 was followed with the exception that red (Moroccan) clay powder was incorporated instead of bentonite clay powder. One teaspoon of glycerin per pint of the resulting mixture was added. The result was a composition similar to that of Example 1. The embodiment of this Example 12a was as effective as that of Example 1 when applied shortly after mixture.

Example 12b Packing Composition

The method described in Example 1 was followed with the exception that green (French) clay powder was incorporated instead of bentonite clay powder. One teaspoon of mineral oil per pint of the resulting mixture was added. The result was a composition similar to that of Example 1. The embodiment of this Example 12b was as effective as that of Example 1 when applied shortly after mixture.

Example 13 Packing Composition 1 quart of sodium bicarbonate was mixed with 1 quart clay, and 1 quart copper sulfate pentahydrate. These three powders were mixed together. 1 quart of vinegar was added to trigger a chemical reaction. The mixture was consistently stirred to break up any clumps until the chemical reaction died down. A second quart of vinegar was added and the mixture was continuously stirring until the chemical reaction ended. Similar to other formulas, heat causes it to break down and separate at a lesser degree. The product must be stored in a dark or cool place and refrigeration recommended. The embodiment of this Example 13 was as effective as that of Example 1 when applied shortly after mixture.

Example 14 Liquid Composition

Two quarts of powdered kaolin clay were combined with two quarts of copper sulfate, pentahydrate. To that mixture, two quarts of sodium bicarbonate were added. The resulting powder was thoroughly mixed. Two quarts of tap water were slowly added while rapidly stirring throughout the entire visible chemical reaction of the powder ingredients to the water. Once the substance was completely mixed and there was no further visible chemical reaction, one cup of magnesium sulfate was added to the mixture. Two quarts of vinegar were then poured slowly while again, quickly stirring until the mixture is consistent and all ingredients mixed. After the ingredients were completely mixed and there were no visible signs of further chemical reactions, the mixture was then refrigerated to cool. When the mixture was cool to the touch, xanthan gum was added in an amount of one tablespoon per quart of mixture and mixed into the composition.

Example 15 Liquid Composition 1 cup bentonite kaolin clay powder was combined with 1 cup copper sulfate pentahydrate, 1 cup sodium bicarbonate, 1 tablespoon of magnesium sulfate, 1 tablespoon sodium borate and 1 tablespoon of zinc oxide. The resulting powder was thoroughly mixed. 1.5 cups of vinegar were slowly added with constant stirring. When the chemical reaction weakens 1 cup of water was slowly added with continuous stirring until the product had no clumps.

Example 16 Liquid Composition

Mix 1 cup kaolin clay powder with 1 cup copper sulfate pentahydrate, 1 cup sodium bicarbonate, 1 tablespoon of magnesium sulfate, 1 tablespoon sodium borate and 1 tablespoon of zinc oxide. Stir until all powders are thoroughly mixed. Slowly add 1.5 cups of vinegar while stirring. When the chemical reaction weakens slowly add 1 cup of water and continue stirring until the product has no clumps of powder. The final product should be a thick liquid. The formula above is designed to treat the outside of the hooves, toe nails, claws to treat conditions caused by bacteria and/or fungi.

Example 17 Liquid Composition

Mix 1 pint bentonite clay powder with 1 pint copper sulfate pentahydrate, 1 pint sodium bicarbonate, 2 tablespoons of magnesium sulfate, 2 tablespoons of zinc oxide, and 2 tablespoons of stearic acid. Stir until all powders are thoroughly mixed. Slowly add 3 cups of vinegar while stirring. When the chemical reaction weakens slowly add 2 cups of water and continue stirring until the product has no clumps of powder. The final product should be a thick salve or cream-like substance. The formula above is designed to treat the outside of the hooves, nails, claws to treat conditions caused by bacteria and/or fungi.

The addition of approximately one teaspoon of xanthan gum per pint of mixture will convert the composition to a clay-like composition.

Example 18 Liquid Composition

Mix 1 pint bentonite clay powder with 1 pint copper sulfate pentahydrate, 1 pint sodium bicarbonate, 2 tablespoons of magnesium sulfate, 2 tablespoons of zinc oxide, and 2 tablespoons of feldspar. Stir until all ingredients are thoroughly mixed. Slowly add 3 cups of acetic acid while stirring. When the chemical reaction weakens slowly add 2 cups of water and continue stirring until the product has no clumps of powder. The final product should be a thick salve or cream-like substance. The formula above is designed to treat fungal infections and cysts on mammals' skin, hooves, nails, and/or claws.

Example 19 Topical Composition

Mix 1 pint bentonite clay powder with 1 pint copper sulfate pentahydrate, 1 pint sodium bicarbonate, 2 tablespoons of magnesium sulfate, 2 fluid ounces of tea tree oil. Stir until all ingredients are thoroughly mixed. Slowly add 2 cups of acetic acid while stirring. When the chemical reaction weakens slowly add 2 cups of betadine. When thoroughly mixed, add 1 cup of water and continue stirring until the product has no clumps of powder. The final product should be a thick salve or cream-like substance. The formula above is designed to treat fungal infections and cysts on mammals' hooves, skin, nails, and/or claws.

Example 20 Topical Composition

Mix 1 cup kaolin clay powder with ⅓ cup copper sulfate pentahydrate, 1 cup sodium bicarbonate, ⅓ cup charcoal powder, and 1 tablespoon of magnesium sulfate. Stir until all ingredients are thoroughly mixed. Slowly add ½ cup of acetic acid while stirring. When the chemical reaction weakens slowly add 1 cup of water and continue stirring until the product has no clumps of powder. The final product should be a thick salve or cream-like substance. The formula above is designed to be used topically as, e.g., a facial mask.

Example 21 Liquid Composition

Mix 2 quarts of copper sulfate pentahydrate, sodium bicarbonate, and bentonite clay powder. Then add 2 cups of magnesium sulfate and mix them all together. Pour 2 quarts of acetic acid in slowly while stirring. Finally, pour 6 quarts of water in while stirring until the chemical reaction settles. The final product should be stored in away from sunlight and/or temperatures over 70 degrees Fahrenheit. This formulation was used to treat hoof rot in cows Example 21 Cooling Composition Mix 1 quart kaolin clay powder with ½ quart copper sulfate pentahydrate, ½ quart sodium bicarbonate, and 2 cups magnesium sulfate. Stir until all ingredients are thoroughly mixed. Slowly add 2 cups of acetic acid while stirring. When the chemical reaction weakens slowly add ¾ quart of acetic acid. When thoroughly mixed, add ½ cup of propylene glycol and continue stirring until the product has no clumps of powder. When thoroughly mixed, add 1 pint of water. The final product is designed to replace ice in ice boots for foundering horses.

The various packing composition embodiments were utilized as a packing material for microbial infections, specifically thrush. Each of these embodiments were used as a packing material on horses exhibiting symptoms of thrush or diagnosed with thrush by a veterinarian. The horse's hooves were first cleaned with a hoof brush to remove debris. The composition was then placed or "packed" in the hoof. Once applied, the horse or animal may remain in normal stall or turnout conditions without worry of contact with manure, urine, or other moist, damp organic matter.

The various liquid composition embodiments were utilized as a topical treatment for infections on the claw of a canine or exterior of a horse's hoof. The material was applied directly on the infected area for a time period sufficient to treat the infection.

The foregoing is illustrative of the present invention, and is not to be construed as limiting thereof. The invention is defined by the following claims, with equivalents of the claims to be included therein.

The invention claimed is:

1. A composition comprising by weight about 18% copper sulfate, about 17% clay, about 16% sodium bicarbonate, and about 22% added water.

* * * * *